United States Patent
McManus et al.

(10) Patent No.: US 9,097,611 B2
(45) Date of Patent: Aug. 4, 2015

(54) FLUID STORAGE AND DISPENSING SYSTEM INCLUDING DYNAMIC FLUID MONITORING OF FLUID STORAGE AND DISPENSING VESSEL

(75) Inventors: James V. McManus, Bethel, CT (US); James Dietz, Allison Park, PA (US); Steven M. Lurcott, Sherman, CT (US)

(73) Assignee: ENTEGRIS, INC., Billerica, MA (US)

( * ) Notice: Subject to any disclaimer, the term of this patent is extended or adjusted under 35 U.S.C. 154(b) by 276 days.

(21) Appl. No.: 13/155,237

(22) Filed: Jun. 7, 2011

(65) Prior Publication Data

US 2011/0232367 A1 Sep. 29, 2011

Related U.S. Application Data

(63) Continuation of application No. 10/972,542, filed on Oct. 25, 2004, now Pat. No. 7,955,797.

(51) Int. Cl.
*B82Y 10/00* (2011.01)
*G01M 3/32* (2006.01)
*F17C 11/00* (2006.01)
*G01F 22/02* (2006.01)

(52) U.S. Cl.
CPC ............. *G01M 3/3236* (2013.01); *F17C 11/00* (2013.01); *G01F 22/02* (2013.01); *G01M 3/32* (2013.01)

(58) Field of Classification Search
CPC ...................................................... B82Y 21/00
See application file for complete search history.

(56) References Cited

U.S. PATENT DOCUMENTS

| | | | |
|---|---|---|---|
| 3,698,249 A | 10/1972 | Weaver | |
| 4,257,260 A | 3/1981 | Beatson et al. | |
| 4,420,980 A | 12/1983 | Dunemann et al. | |
| 4,546,649 A | 10/1985 | Kantor | |
| 4,606,497 A | 8/1986 | Heimovics, Jr. | |
| 4,865,210 A | 9/1989 | Brainard, II | |
| 4,905,855 A | 3/1990 | Troiano et al. | |
| 5,146,098 A * | 9/1992 | Stack | 250/492.2 |
| 5,179,981 A | 1/1993 | Hicks et al. | |
| 5,383,352 A * | 1/1995 | Krawetz et al. | 73/54.01 |
| 5,413,159 A | 5/1995 | Olney et al. | |
| 5,493,903 A | 2/1996 | Allen | |
| 5,505,092 A | 4/1996 | Kowalski | |

(Continued)

OTHER PUBLICATIONS

Hottinger Baldwin Messtechnik, "Strain gauges and accessories (Downloaded from: http://www.hbm.com/data/softdoc/hbm/data/s1265.pdf)", Jul. 18, 2006, pp. 263, Publisher: Hottinger Baldwin Messtechnik, Wagetechnik GmbH.

*Primary Examiner* — Zandra Smith
*Assistant Examiner* — Andre' C Stevenson
(74) *Attorney, Agent, or Firm* — Hultquist, PLLC; Steven J. Hultquist; Rosa Yaghmour (57) ABSTRACT

A monitoring system for monitoring fluid in a fluid supply vessel during operation including dispensing of fluid from the fluid supply vessel. The monitoring system includes (i) one or more sensors for monitoring a characteristic of the fluid supply vessel or the fluid dispensed therefrom, (ii) a data acquisition module operatively coupled to the one or more sensors to receive monitoring data therefrom and responsively generate an output correlative to the characteristic monitored by the one or more sensors, and (iii) a processor and display operatively coupled with the data acquisition module and arranged to process the output from the data acquisition module and responsively output a graphical representation of fluid in the fluid supply vessel.

17 Claims, 2 Drawing Sheets

(56) References Cited

U.S. PATENT DOCUMENTS

| | | | |
|---|---|---|---|
| 5,518,528 A * | 5/1996 | Tom et al. | 95/103 |
| 5,597,085 A | 1/1997 | Rauworth et al. | |
| 5,704,965 A | 1/1998 | Tom et al. | |
| 5,704,967 A | 1/1998 | Tom et al. | |
| 5,707,424 A | 1/1998 | Tom et al. | |
| 5,882,384 A | 3/1999 | Tom et al. | |
| 5,883,305 A | 3/1999 | Jo et al. | |
| 6,019,823 A | 2/2000 | Tischler et al. | |
| 6,070,576 A | 6/2000 | Banucci et al. | |
| 6,073,759 A | 6/2000 | Lamborne et al. | |
| 6,079,252 A | 6/2000 | Tabler et al. | |
| 6,089,027 A | 7/2000 | Wang et al. | |
| 6,101,816 A | 8/2000 | Wang et al. | |
| 6,124,787 A | 9/2000 | Isakov et al. | |
| 6,132,492 A | 10/2000 | Hultquist et al. | |
| 6,156,578 A | 12/2000 | Tom | |
| 6,196,052 B1 * | 3/2001 | May et al. | 73/24.06 |
| 6,204,180 B1 | 3/2001 | Tom et al. | |
| 6,295,861 B1 | 10/2001 | Tom et al. | |
| 6,338,312 B2 | 1/2002 | Hayes et al. | |
| 6,343,476 B1 | 2/2002 | Wang et al. | |
| 6,360,546 B1 | 3/2002 | Wang et al. | |
| 6,391,385 B1 | 5/2002 | Holst et al. | |
| 6,406,519 B1 | 6/2002 | Tom et al. | |
| 6,453,924 B1 | 9/2002 | Wang et al. | |
| 6,474,076 B2 | 11/2002 | Wang et al. | |
| 6,494,343 B2 * | 12/2002 | McManus et al. | 222/55 |
| 6,500,238 B1 | 12/2002 | Brandes et al. | |
| 6,514,399 B1 | 2/2003 | Parce et al. | |
| 6,540,814 B2 * | 4/2003 | Hayes et al. | 95/116 |
| 6,540,819 B2 | 4/2003 | Tom et al. | |
| 6,561,213 B2 | 5/2003 | Wang et al. | |
| 6,581,623 B1 | 6/2003 | Carpenter et al. | |
| 6,592,653 B2 | 7/2003 | Wang et al. | |
| 6,660,063 B2 | 12/2003 | Tom et al. | |
| 6,716,271 B1 | 4/2004 | Arno et al. | |
| 6,749,671 B2 | 6/2004 | Holst et al. | |
| 6,805,728 B2 | 10/2004 | Sweeney et al. | |
| 6,843,830 B2 | 1/2005 | Sherer | |
| 6,939,394 B2 | 9/2005 | Carruthers | |
| 6,947,138 B2 | 9/2005 | Arno | |
| 6,955,198 B2 | 10/2005 | Wodjenski | |
| 6,991,671 B2 | 1/2006 | Brestovansky et al. | |
| 6,997,202 B2 | 2/2006 | Olander | |
| 7,018,448 B2 | 3/2006 | Wodjenski et al. | |
| 7,063,097 B2 | 6/2006 | Arno et al. | |
| 7,104,292 B2 | 9/2006 | Wodjenski | |
| 7,105,037 B2 | 9/2006 | Olander et al. | |
| 7,118,445 B2 | 10/2006 | Moore et al. | |
| 7,235,214 B2 | 6/2007 | Rodier et al. | |
| 7,275,420 B2 | 10/2007 | Discenzo | |
| 7,955,797 B2 | 6/2011 | McManus et al. | |
| 7,966,879 B2 | 6/2011 | Dietz et al. | |
| 2002/0103563 A1 | 8/2002 | Izawa et al. | |
| 2002/0190283 A1 | 12/2002 | Seno et al. | |
| 2003/0029224 A1 | 2/2003 | Pratt et al. | |
| 2004/0251484 A1 | 12/2004 | Miyazaki et al. | |
| 2005/0008908 A1 | 1/2005 | Kaye et al. | |
| 2005/0255442 A1 | 11/2005 | Brassil et al. | |
| 2006/0091385 A1 | 5/2006 | Mair et al. | |
| 2006/0169033 A1 * | 8/2006 | Discenzo | 73/64.56 |
| 2008/0017104 A1 | 1/2008 | Matyushkin et al. | |
| 2011/0252883 A1 | 10/2011 | Dietz et al. | |

* cited by examiner

FLUID STORAGE AND DISPENSING SYSTEM INCLUDING DYNAMIC FLUID MONITORING OF FLUID STORAGE AND DISPENSING VESSEL

CROSS REFERENCE TO RELATED APPLICATIONS

This is a continuation under 35 USC 120 of U.S. patent application Ser. No. 10/972,542 filed Oct. 25, 2004, and issued Jun. 7, 2011 as U.S. Pat. No. 7,955,797. The disclosure of U.S. patent application Ser. No. 10/972,542 is hereby incorporated herein by reference in its entirety, for all purposes.

FIELD OF THE INVENTION

The present invention relates to a fluid storage and dispensing system including dynamic monitoring of inventory of a fluid storage and dispensing vessel.

DESCRIPTION OF THE RELATED ART

In the field of semiconductor manufacturing, involving unit operations such as ion implantation, chemical vapor deposition, spin-on coating, etching, cleaning of process chambers, treatment of effluents, etc., it is common to utilize specialized fluid reagents of widely varying character.

Due to the high costs, significant toxicity, and ultra-high purity requirements of many of such fluid reagents, a variety of dedicated source vessels and containment apparatus have come into widespread usage in semiconductor manufacturing facilities. In many instances, these specialty fluid supply apparatus, which have replaced conventional gas cylinders in such service, are accessorized with various fluid monitoring and control devices. Such devices may for example include leak detection monitors, pressure transducers in dispensing lines, temperature sensors for ensuring that contained and dispensed fluid is at an appropriate thermal state for the associated process operation, mass flow controllers, restricted flow orifice elements, and the like.

Among the most innovative and commercially successful of the current generation of fluid storage and dispensing systems for semiconductor manufacturing reagents are those commercialized by ATMI, Inc. (Danbury, Conn.) under the trademarks SDS® and VAC®.

The SDS® fluid storage and dispensing system includes a vessel containing a solid-phase sorbent material having sorptive affinity for the semiconductor manufacturing fluid reagent, whereby fluid stored in the vessel on such sorbent material can be selectively desorbed therefrom and dispensed from the vessel under dispensing conditions. The semiconductor reagent fluid can be stored at low pressure as a result of its sorptive retention in the vessel, e.g., at subatmospheric pressures. As a result of such low pressure storage, a high level of safety is provided, in relation to high pressure gas cylinders in which a valve head failure can result in widespread dissemination of the fluid contents of the cylinder. The SDS® fluid storage and dispensing system is variously described in U.S. Pat. Nos. 5,518,528; 5,704,965; 5,704,967; and 5,707,424.

The VAC® fluid storage and dispensing system includes a vessel containing a semiconductor manufacturing fluid reagent and equipped with a pressure regulator that is interiorly disposed in the vessel and in flow communication with a dispensing assembly for dispensing of fluid at pressure determined by the set point of the pressure regulator. The pressure regulator set point can be set to a low dispensing pressure level. The VAC® fluid storage and dispensing system is variously described in U.S. Pat. Nos. 6,101,816; 6,089,027; 6,360,546; 6,474,076; and 6,343,476.

By its interior pressure regulator configuration, the VAC® fluid storage and dispensing system achieves an enhancement of safety in the containment of high pressure fluids, since the regulator prevents the discharge of fluid at pressure above the regulator set point, and since the regulator is inside the vessel and thereby protected from ambient contamination and direct impact.

In ion implant applications, the SDS® fluid storage and dispensing system has become a standard gas source in the semiconductor manufacturing industry. Currently, it is estimated that approximately 80% of the installed base of 4000 ion implant units worldwide utilize the SDS® fluid storage and dispensing system.

In order to assure proper utilization of the SDS® fluid storage and dispensing system, special consideration of the gas delivery system design including low pressure drop components and accurate measurement of sub-atmospheric (torr-level) pressure is required. This poses a particular problem in that there are a half dozen or so major manufacturers of ion implant equipment. Each manufacturer makes several model types and new products are released every 2-3 years. This circumstance results in a wide variety of ion implant systems and subsequently results in a myriad of gas monitoring techniques being in use, many of which are inadequate or otherwise inefficient and unstandardized.

In one of the most popular current ion implant system designs, gas monitoring of the inventory of fluid in the SDS® fluid storage and dispensing system requires navigating through a complex series of software files in order to determine pressure of the fluid in the SDS® fluid storage and dispensing vessel. The user then has to manually convert the pressure into a unit of fluid utilization. The problem with this approach is that the time required to navigate the software screens in this implementation is excessive, and most ion implant operators and technicians cannot understand the conversion mathematics required to convert the pressure reading into a meaningful utilization expression.

The foregoing deficiencies in monitoring utilization of fluid stored for dispensing in the fluid supply vessel is exacerbated by the fact that numerous implanter units, e.g., 5-20, are provided in a typically-sized semiconductor manufacturing facility, or "fab." The multiplicity of such units means that it often requires an operator or technician to spend hours in monitoring operations for all of the implanter units to determine the rate and extent of fluid consumption by the ion implanter, or other dispensed fluid-using equipment in the semiconductor fab.

Another problem with conventional approaches to monitoring fluid utilization for determining consumption of the fluid in the fluid supply vessel is that it is difficult to predict and alert fab personnel to the approaching end-point of the dispensing operation, when the vessel is nearly depleted of its fluid contents and approaching exhaustion.

Since existing approaches to determination of utilization are poor, it is a not infrequent occurrence that fab personnel run out of fluid without warning during active implant operation. This occurrence typically has a severe impact on fab productivity since the implant unit must then be shut down to accommodate change-out of the depleted fluid supply and dispensing vessel, and installation of a fresh vessel containing fluid for renewed operation. Since this occurrence is unscheduled, the efficiency with which the fluid storage and dispensing system can be replaced is less than if the event were scheduled or able to be predicted.

There is therefore a significant need in the art for a fast, accurate and reliable approach to monitoring utilization and detecting end-point dispensing conditions in the use of fluid storage and dispensing systems of the above-described type.

SUMMARY OF THE INVENTION

The present invention relates generally to a system and method for dynamic monitoring of fluid in fluid storage and dispensing systems, such as those of the SDS®-type and the VAC®-type, to determine utilization of fluid in such systems.

In one aspect, the present invention relates to a monitoring system for monitoring fluid in a fluid supply vessel during operation including dispensing of fluid from the fluid supply vessel, said monitoring system including (i) one or more sensors for monitoring a characteristic of the fluid supply vessel or the fluid dispensed therefrom, (ii) a data acquisition module operatively coupled to the one or more sensors to receive monitoring data therefrom and responsively generate an output correlative to the characteristic monitored by the one or more sensors, and (iii) a processor and display operatively coupled with the data acquisition module and arranged to process the output from the data acquisition module and responsively output a graphical representation of fluid in the fluid supply vessel.

In another aspect, the invention relates to a method of monitoring fluid in a fluid supply vessel during operation including dispensing of fluid from the fluid supply vessel, said method including (i) monitoring a characteristic of the fluid supply vessel or the fluid dispensed therefrom, (ii) acquiring data from said monitoring and responsively generating an output correlative to the monitoring characteristic, and (iii) processing the output from the data acquiring and responsively outputting a graphical representation of fluid in the fluid supply vessel.

Other aspects, features and advantages of the invention will be more fully apparent from the ensuing disclosure and appended claims.

DETAILED DESCRIPTION OF THE INVENTION AND PREFERRED FEATURES THEREOF

The present invention provides a dynamic monitoring system and method that is usefully employed to monitoring fluid utilization in a fluid supply system, such as the fluid storage and dispensing systems of the types described in the Background of the Invention section hereof.

The monitoring system includes (i) one or more sensors for monitoring a characteristic of the fluid supply vessel or the gas dispensed therefrom, (ii) a data acquisition module operatively coupled to the one or more sensors, and (iii) a processing and display unit operatively coupled to the data acquisition module for determining utilization of the fluid in the fluid supply vessel and responsively outputting a graphical representation of fluid in the fluid supply vessel.

The one or more sensors for monitoring a characteristic of the fluid supply vessel in the dynamic fluid monitoring system of the invention may be of any suitable type, such as fluid sensors for sensing a selected characteristic of the fluid that is useful in determining the inventory and utilization rate of the gas. The selected characteristic of the fluid may for example include pressure of the fluid, concentration of a specific component of the fluid, temperature of the fluid, flow rate of the fluid, mixture of gases, pressure of the fluid, flow rate of purging gases, etc., and the corresponding sensors may variously include pressure transducers, manometric pressure sensors, thermocouples, mass flow controllers, flow totalizers, etc.

Alternatively, the one or more monitoring sensors in the dynamic monitoring system of the invention may include one or more sensors for determining a characteristic of the fluid supply vessel itself, such as for example strain on the vessel wall of the fluid supply vessel where the fluid is contained at high pressure in the vessel, e.g., a vessel such as that of the VAC® fluid supply system (ATMI, Inc., Danbury, Conn., USA) described earlier herein, wherein the fluid is confined against a pressure regulator set to a predetermined set point pressure for dispensing of fluid from the vessel. Alternatively, the characteristic of the fluid supply vessel that may be employed for monitoring in accordance with the invention can be temperature of the fluid supply vessel, displacement or flexial character of the vessel, weight of the fluid supply vessel containing the fluid being or to be dispensed, etc. Still further, other devices that may be monitored include any pressure-reducing device that has a net effect in decreasing the interior pressure of a cylinder thereby reducing downstream pressure, such as restrictive flow orifice. Thus, by monitoring this type of device the operator would be assured that delivery pressures remained fixed and gas flow rates more closely matched the actual process needs downstream.

The processing and display unit that is coupled to the data acquisition module may utilize any suitable processing means, e.g., a general purpose programmable digital computer or central processing unit (CPU) including memory and processor components. The processor may be arranged to communicate with the memory by means of an address/data bus, and can be constituted by a commercially available or custom microprocessor. The memory can include, without limitation, devices of varied type, such as cache, ROM, PROM, EPROM, EEPROM, flash memory, SRAM, and DRAM.

The memory may include several categories of software and data used in the data processing system: the operating system; the application programs; the input/output (I/O) device drivers and the data. The data may include a database of known profiles of fluid storage and dispensing vessel characteristics, characteristics of various fluids, historical operating data for the gas-utilizing equipment being supplied with gas from the fluid storage and dispensing system, etc.

It will be appreciated that the operating system in the processing and display unit can be of any suitable type for use with a data processing system. Illustrative examples of operating systems that can be usefully employed include, without limitation, OS/2, AIX, OS/390 or System390 (International Business Machines Corporation, Armonk, N.Y.), Windows CE, Windows NT, Windows95, Windows98, Windows2000, or WindowsXP (Microsoft Corporation, Redmond, Wash.), Unix or Linux or FreeBSD, Palm OS from Palm, Inc., Mac OS (Apple Computer, Inc.), LabView or proprietary operating systems.

The I/O device drivers typically include software routines accessed through the operating system by the application programs to communicate with devices such as I/O data port(s), data storage and certain components of the memory.

The application programs are illustrative of the programs that implement the various features of the system and can suitably include one or more applications that support analysis of the data. The data represent the static and dynamic data used by the application programs, the operating system, the I/O device drivers, and other software programs that may reside in the memory.

Any configuration of the processor capable of carrying out the operations for the methodology of the invention can be advantageously employed.

The I/O data port of the processing and display unit can be used to transfer information between the processing and display unit and another computer system or a network (e.g., the Internet) or to other devices controllable by the processor.

The processing and display unit includes a display for graphically outputting the fluid utilization of the vessel(s) being monitored, e.g., in the form of a representation of the vessel(s) being monitored and its fluid content. This representation may be a "gas gauge" type of graphic depiction, in which the fluid content is shown in scale to the vessel schematically depicted in the graphical output, as a two-dimensional column having an upper bounding line representing the volumetric content of the fluid in the vessel, in which the upper bounding line is vertically downwardly translated in the display as the fluid is dispensed from the vessel and consumed in the external fluid-consuming facility that is being supplied with fluid from the vessel. Such type of depiction of the "fill status" of the vessel provides an intuitive and readily visually perceptible indication of the inventory of the fluid remaining in the vessel.

In a specific embodiment, the dynamic monitoring system of the invention may be employed to monitor an SDS® gas supply system, by monitoring pressure signals from pressure transducers operatively arranged to detect the pressure characteristic of gas being dispensed from the SDS® vessel. In another specific embodiment, the dynamic monitoring system may be employed to monitor a VAC® gas supply system, by monitoring a strain gauge on the VAC® vessel inside an ion implanter. The sensor-derived signals then are sent to the data acquisition module, from which send signals can be sent via a signal transmission line, e.g., a fiber optic communications link, to the processing and display unit, for display and archiving of the data in a nonvolatile buffer.

In another embodiment, the processing and display unit may also incorporate or be linked to alarming means, such as for example low pressure alarms indicating that the fluid storage and dispensing vessel is approaching a depletion end point.

The data acquisition module and the processing and display unit may be constructed and arranged to monitor multiple fluid supply and dispensing vessels, such as an array of such vessels in the gas box of an ion implanter in a fab.

The processing and display unit is suitably configured in one embodiment of the invention to calculate remaining usable volume of fluid in a fluid supply vessel based on known isotherm equations, vessel size and fluid type. This is highly advantageous because the volume of fluid remaining in a fluid supply vessel as it approaches exhaustion is not linear with pressure. As an illustrative example, with 100 ton of fluid pressure remaining in a 2.2 L $AsH_3$ SDS® cylinder, 50% of the deliverable arsine still remains in the vessel.

Figure 1:
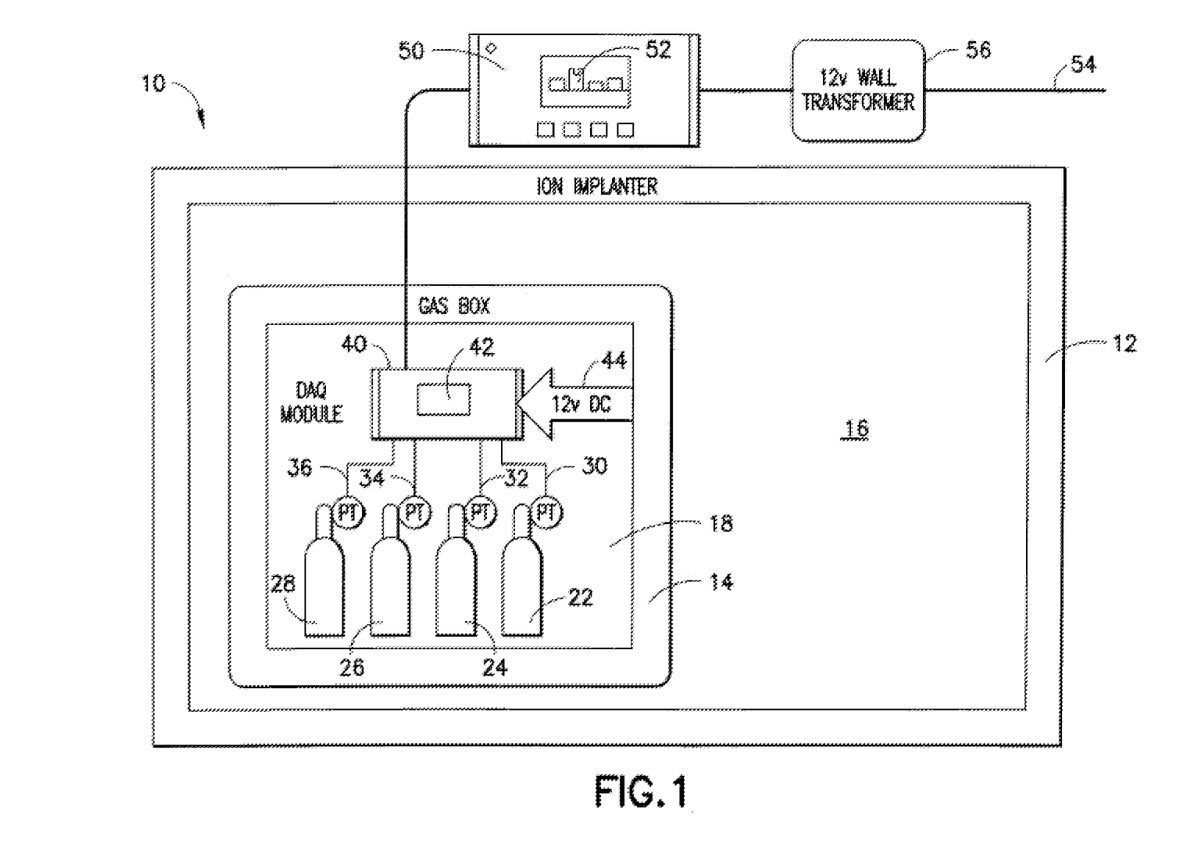
FIG. 1 is a schematic representation of an ion implanter utilizing an arrangement of fluid storage and dispensing vessels in the gas box of the implanter, in which fluid utilization is dynamically monitored by a fluid monitoring system, according to one embodiment of the invention.

Referring now to the drawings, FIG. 1 is a schematic representation of a fab installation 10 including an ion implanter 12 utilizing an arrangement of fluid storage and dispensing vessels 22, 24, 26 and 28 in the gas box 14 of the implanter, in which fluid utilization is dynamically monitored by a fluid monitoring system, according to one embodiment of the invention.

As schematically illustrated, the ion implanter 12 includes a containment structure defining an interior volume 16 containing the gas box 14. The gas box in turn defines an interior volume 18 in which is disposed an array of fluid storage and dispensing vessels 22, 24, 26 and 28, each of which has an associated pressure transducer ("PT"), e.g., disposed in a valve head of the vessel assembly and arranged to sense the fluid pressure of fluid dispensed from the associated vessel.

The pressure transducers associated with the vessels 22, 24, 26 and 28 generate signals correlative to the sensed pressure in each dispensing operation (the flow circuitry associated with the fluid supply and dispensing vessels, and the details of the ion implantation apparatus in the ion implanter containment structure not being shown, for ease of description) and such signals are transmitted by the signal transmission lines 30, 32, 34 and 36 to the data acquisition module 40.

The data acquisition module comprises a housing 42 containing associated electronics and acquisition hardware, in a unitary configuration. The data acquisition module 40 receives power from a suitable power supply (e.g., a 12 volt DC supply) schematically indicated by arrow 44 in FIG. 1.

The data acquisition module 40 serves to acquire the sensing signals from the sensors associated with the vessels and process the signals into a suitable form for transmission to the processor and display unit 50 by means of signal transmission line 48, such as a fiber optic cable, extending from the data acquisition module 40 through the wall of the gas box 14 and the enclosing wall of the ion implanter 12, to the processor and display unit 50.

The processor and display unit 50 includes signal processing means as previously described herein, which processes the signals transmitted by the signal transmission line 48 to produce a graphical output that is displayed on the display 52 of the unit 50. The processor and display unit 50 is powered by a suitable power supply, e.g., by a power cord 54 operatively coupled with a transformer 56, e.g., a 12 volt wall transformer, and adapted for plug-in to a wall socket of an electrical supply network, e.g., a 110-volt or 220-volt service.

Figure 2:
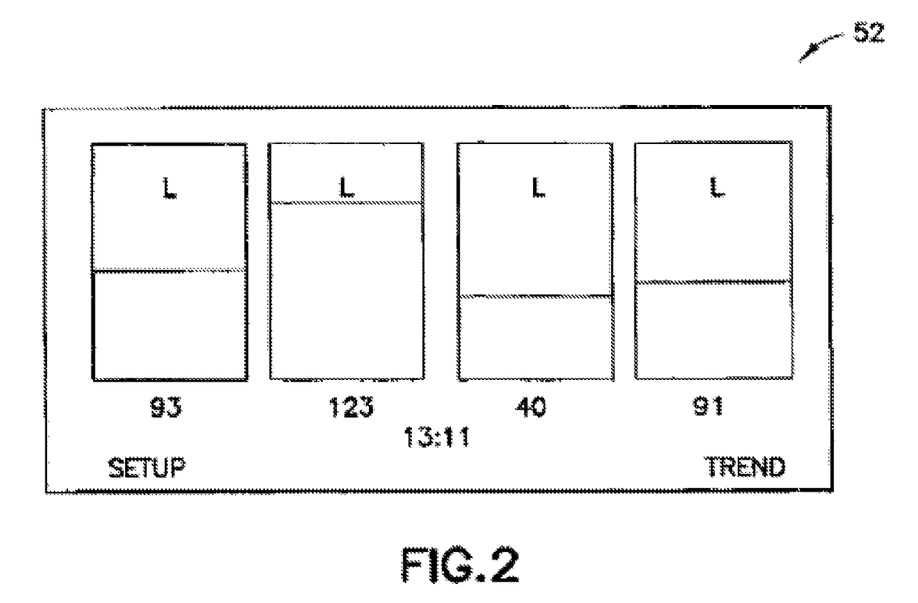
FIG. 2 is a schematic representation of the visual display interface of a visual display unit of the fluid monitoring system shown in FIG. 1.

FIG. 2 is a schematic representation of the visual display interface of the visual display unit 50 of the fluid monitoring system in the fab installation 10 shown in FIG. 1.

As illustrated, the visual display interface shows graphical depictions of each of the four vessels 22, 24, 26 and 28 in the gas box 14 of the installation 10, in the form of two-dimensional vertically extending rectangles having a horizontal line depicting the boundary of the fluid inventory in each rectangle.

In the specific example shown, the fluid inventory is shown by a white "fill volume" which in relation to the total area of the associated rectangle indicates the amount of the fluid remaining in the vessel at any given time. By such output, the status of each of the monitored vessels is readily apparent at a glance, as to its fluid inventory. The display may also, as in the illustrative display shown in FIG. 2, also provide a numerical indication of the relative fluid filled state of the respective vessels (e.g., as shown by the numerical indicia "93", "123", "40" and "91" in the display depicted in FIG. 2).

The monitoring process may be carried out in any suitable manner, as regards transmission of sensed data to the data acquisition module 40, for monitoring in a real-time, continuous fashion as desired in a given application of the invention.

Regarding specific embodiments of the dynamic monitoring system shown in FIG. 1 and FIG. 2, the processor and display unit may be equipped for interfacing with a computer, e.g., in an operator station in the fab. The processor and display unit may for example be equipped with an RS-232 port for such purpose, to enable cabling between such RS-232 port on the processor and display module, and a serial port on an operator computer. The data acquisition module may be suitably configured for providing sensor excitation and analog input for each of the sensors associated with the vessels. When the sensors are strain gauges mounted on the walls of the fluid storage and dispensing vessels, such sensors may be readily cabled to the data acquisition module.

The processor and display unit in a specific embodiment is arranged for data logging with archiving of up to 3000 data points, with logging rates configured from a setup menu to a suitable value in a range of from 5 seconds per point to 2 hours per point. All four channels for the four vessels in the illustrative installation are logged and logging data is downloadable through an RS-232 port of the processor and display unit. A trend graph may be provided for each of the four monitored channels, scaled to match the bar graph 100% (indicating complete fluid inventory in the vessel) and to show the entire data log buffer. Since the display is 100 points wide and the data log is 3000 points wide, the display shows an average of 300 readings per pixel on the display. For finer viewing, data may be downloaded from the processor and display unit via the RS232 port. The processor and display unit in a specific embodiment is configured so that each data element is time stamped by the processor.

The features, operation and advantages of the invention are more fully described with reference to the following non-limiting example of an illustrative embodiment of the invention.

EXAMPLE

This example illustrates the procedures used to estimate the usable gas in a gas storage and dispensing system of a type commercially available under the trademark SDS2 from ATMI, Inc. (Danbury, Conn.) and more fully described in U.S. Pat. Nos. 5,518,528; 5,704,965; 5,704,967; and 5,707,424. Such gas storage and dispensing system includes a gas storage and dispensing vessel containing a bead activated carbon adsorbent having sorptive affinity for the semiconductor manufacturing gas held in the interior volume of the vessel. The gas may be of any suitable type, e.g., arsine, phosphine, boron trifluoride, germanium tetrafluoride, and silicon tetrafluoride, and the gas may be retained in the vessel for dispensing therefrom at suitable pressure, e.g., a subatmospheric pressure in a range of 200 to 700 torr.

The illustrative gas storage and dispensing system is deployed in an ion implanter of the type schematically shown in FIG. 1 hereof, equipped with a dynamic fluid utilization monitoring system of the invention. The dynamic fluid monitoring system in this embodiment includes a processing and display unit, a data acquisition module, and fluid sensors for sensing a selected characteristic of the fluid that may be used to determine the inventory and utilization rate of the gas. The fluid sensors in this embodiment include pressure transducers, each of which is operatively coupled with one of the multiple gas storage and dispensing vessels as schematically shown in FIG. 1.

The processing and display unit is programmably arranged to estimate the amount of usable gas remaining in the SDS2 vessel at a given pressure and temperature. The dynamic monitoring system of the invention can be used to estimate the service life of a gas storage and dispensing vessel used in the implanter.

In the utilization determination, the following symbols and units are employed.
T Gasbox temperature, ° C.
P Pressure transducer reading, ton or mmHg
$P_{21}$ Normalized pressure reading, ton or mmHg
$P_{end-12}$ Normalized end point pressure, ton or mmHg
$C_{lo}$ Pressure change per degree ° C. when temperature is less than 21° C., torr/° C.
$C_{mid}$ Pressure change per degree ° C. when temperature is between 21-26° C., torr/° C.
$C_{hi}$ Pressure change per degree ° C. when temperature is less than 26-33° C., torr/° C.
$C_{end-lo}$ Pressure change per degree ° C. for end point pressure (less than 21° C.), torr/° C.
$C_{end-mid}$ Pressure change per degree ° C. for end point pressure (21-26° C.), torr/° C.
$C_{end-hi}$ Pressure change per degree ° C. for end point pressure (26-33° C.), torr/° C.
CW Carbon weight in the cylinder, gram
MW Molecular weight of the gas
sccm Gas flow rate to the ion source, ml/min
G The amount gas in grams remained in the cylinder, gram
V The amount gas in cubic centimeter remained in the cylinder, ml
HR Number of hours left before the cylinder is empty, hour.
4× 2.2 liter SDS® cylinder, also called JY size
7× 0.4 liter SDS® cylinder, also called WY size
3× 6.6 liter SDS® cylinder, also called UY size The utilization determination is carried out by the following steps:

Step 1: Measure or determine the implanter gasbox temperature T (° C.)

Step 2: Determine the gas storage and dispensing vessel size and weight of sorbent material therein. For example, the vessel size may be 4×, 7× or 3×. The sorbent then may have a carbon sorbent material disposed in the vessel, having a carbon weight (CW) in grams, which is dependent on the vessel size. If the vessel size is 4×, then the CW is 1275. If the vessel size is 7×, then the CW is 239. If the vessel size is 3×, then the CW is 3825.

Step 3: Set the end-point pressure $P_{end}$ of the fluid storage and dispensing system, e.g., an end-point pressure $P_{end}$ of 5 torr.

Step 4: Measure the vessel pressure read P.

Step 5: Determine the temperature coefficients, dP/dT, at various pressures.

For example:
If T is less than 21° C.:

$$C_{lo}=0.04079168*(P^{0.9623277})$$

If T is between 21 to 26° C.:

$$C_{mid}=0.07282172*(P^{0.8938195})$$

If T is less than 26 to 33° C.:

$$C_{hi}=0.08678193*(P^{0.8914468})$$

Step 6: Determine the temperature coefficient for the end point pressure.
For example:
If T is less than 21° C.:

$$C_{end-lo}=0.04079168*(P_{end}^{0.9623277})$$

If T is between 21 to 26° C.:

$$C_{end-mid}=0.07282172*(P_{end}^{0.8938195})$$

If T is less than 26 to 33° C.:

$$C_{end-hi}=0.08678193*(P_{end}^{-0.8914468})$$

Step 7: Normalize the pressure reading to a predetermined temperature, e.g., 21° C.
For example:
If T is less than 21° C.:

$$P_{21}=P-(T-21)*C_{lo}$$

If T is between 21 to 26° C.:

$$P_{21}=P-(T-21)*C_{mid}$$

If T is between 26 to 33° C.:

$$P_{21}=P-(T-21)*C_{hi}$$

Step 8: Normalize the end point pressure to the predetermined temperature (21° C.).
For example:
If T is less than 21° C.:

$$P_{end-21}=P_{end}-(T-21)*C_{end-lo}$$

If T is between 21 to 26° C.:

$$P_{end-21}=P_{end}-(T-21)*C_{end-mid}$$

If T is between 26 to 33° C.:

$$P_{end-21}=P_{end}-(T-21)*C_{end-hi}$$

Step 9: Determine isotherm equations at the predetermined temperature (21° C.).
For example, for various illustrative gases:
isotherm equations at 21° C.:

$AsH_3$ Capacity (g/g): $f(P)=-0.40857+0.14009*(\ln(P+24.5858))$ $PH_3$ Capacity (g/g): $f(P)=-0.29123+0.06949*(\ln(P+73.89104))$ $BF_3$ Capacity (g/g): $f(P)=0.03949+0.00532*(P^{0.49046})$ $GeF_4$ Capacity (g/g): $f(P)=0.2394*(P^{-0.2139})$ $SiF_4$ Capacity (g/g): $f(P)=-0.60234+0.1223*(\ln(P+160.6716))$ wherein g/g is the gram of gas per gram of carbon, and P is the pressure in torr or mmHg.

Step 10: Determine the amount of gas remaining in the fluid storage and dispensing vessel.
For example:
Weight: Grams of gas remaining in the cylinder (g):

$$G=CW*f(P_{21})-f(P_{end-21})$$

Volume: Cubic Centimeter of Gas remained in the cylinder (ml):

$$V=(G/MW)*22400$$

where
$AsH_3$: MW=78
$PH_3$: MW=34
$BF_3$: MW=68
$GeF_4$: MW=149
$SiF_4$: MW=104

Cylinder life time: Working hours of the cylinder remaining (hr):

$$HR=(V/sccm)/60$$

wherein sccm is the gas flowrate into the ion source (e.g., 2 ml/min)

The foregoing methodology permits the dynamic monitoring of the gas inventory of the fluid storage and dispensing system in a ready, accurate and reproducible manner, that is outputted by the visual display module in a manner illustrated in FIG. 2 hereof, wherein the vertical height of the fluid column on the visual display is indicative of the amount of fluid remaining in the storage and dispensing vessel of such system.

It will therefore be seen that the system and method of the present invention permit a simple visually perceptible indication of the fluid inventory of vessels in a fluid storage and dispensing system, which is simply and easily applicable to the dynamic monitoring of fluid in supply vessels in a gas box of an ion implanter. The invention overcomes the problems of the prior art including the inability to determine with precision the amount of fluid remaining in vessels for active processing, and the approach to exhaustion of fluid in the fluid supply vessels.

As a result, the system and method of the invention permit the uptime of an ion implanter to be maximized, and the change-out of fluid supply vessels to be accurately predicted and scheduled.

Although the invention has been described herein with reference to illustrative features, aspects and embodiments, it will be appreciated that the invention may be practiced with modifications, variations and in other embodiments, as will suggest themselves to those of ordinary skill based on the disclosure herein. The invention therefore is to be interpreted and construed, as encompassing all such modifications, variations, and other embodiments, within the spirit and scope of the claims hereafter set forth.

What is claimed is:

1. A monitoring system for dynamically monitoring the volume of fluid in an adsorbent-based gas supply vessel in a gas box of an ion implanter during operation including dispensing of gas from the gas supply vessel, said monitoring system including (i) a monitoring assembly in the gas box, adapted to monitor at least one characteristic of the gas supply vessel selected from the group consisting of: vessel wall strain; vessel temperature; vessel displacement; vessel flexial character; and vessel weight or at least one characteristic of the gas dispensed from the gas supply vessel selected from group consisting of: gas pressure; gas temperature; cumulative flow volume; and gas flow rate, and transmit an output correlative to the at least one monitored characteristic, and (ii) an output assembly external to the ion implanter, with said monitoring assembly being arranged in signal transmission relationship to the output assembly by a signal transmission arrangement including a signal transmission optical cable extending exteriorly of the ion implanter to the output assembly, wherein the output assembly comprises a processor and a display, and is programmably arranged to provide an output on said display depicting a real-time graphical representation of volume of gas remaining in the gas supply vessel, with the processor being configured to determine, based on isotherm equations, the volume of gas remaining in the gas supply vessel from the output transmitted by the monitoring assembly.

2. The monitoring system of claim 1, wherein the monitoring assembly is adapted to monitor at least one characteristic of the fluid supply vessel.

3. The monitoring system of claim 2, wherein the monitoring assembly is adapted to monitor at least one characteristic of the fluid supply vessel, wherein said at least one characteristic is selected from the group consisting of: vessel wall strain; vessel displacement; vessel flexial character; and vessel weight.

4. The monitoring system of claim 1, wherein the monitoring assembly is adapted to monitor at least one characteristic of the gas dispensed from the gas supply vessel.

5. The monitoring system of claim 4, wherein the monitoring assembly is adapted to monitor at least one characteristic of the gas dispensed from the gas supply vessel, wherein said at least one characteristic is selected from group consisting of: gas pressure, cumulative flow volume; and gas flow rate.

6. The monitoring system of claim 1, wherein the monitoring assembly comprises at least one sensor selected from the group consisting of: pressure transducers, manometric pressure sensors, thermocouples, mass flow controllers, and flow totalizers.

7. A monitoring system for dynamically monitoring the volumetric content of fluid in a fluid supply vessel in a gas box of an ion implanter during operation including dispensing of fluid from the fluid supply vessel, said monitoring system including
(i) a monitoring assembly in the gas box, adapted to monitor at least one characteristic of the fluid supply vessel or the fluid dispensed therefrom, and transmit an output correlative to the at least one monitored characteristic, and
(ii) an output assembly external to the ion implanter, with said monitoring assembly being arranged in signal transmission relationship to the output assembly by a signal transmission arrangement including a signal transmission optical cable extending exteriorly of the ion implanter to the output assembly,
wherein the output assembly comprises a processor and a display, and is programmably arranged to provide an output on said display depicting a representation of the fluid supply vessel with a volumetric content of fluid in the vessel, wherein said volumetric content of fluid is determined by said processor based on the output transmitted by the monitoring assembly, to provide real-time graphical representation of said volumetric content of fluid in the fluid supply vessel,
wherein the fluid supply vessel contains a sorbent for storing the fluid and from which the fluid is selectively desorbed for dispensing, and the monitoring system is adapted to perform the following sequence of operations:
sensing gas box temperature T;
measuring the fluid supply vessel pressure P;
setting an end-point pressure for dispensing fluid from said fluid supply vessel;
determining temperature coefficients dP/dT at various pressures;
determining temperature coefficient for said end-point pressure;
normalizing measured pressure to a predetermined temperature;
normalizing said end-point pressure to said predetermined temperature;
determining isotherm equations at said predetermined temperature for said sorbent and fluid;
determining, using said isotherm equations, the amount of fluid remaining in the fluid supply vessel; and
outputting the amount of fluid remaining in the fluid supply vessel to the display.

8. An ion implanter including a gas box containing at least one gas supply vessel, and a monitoring system as claimed in claim 7, arranged for monitoring fluid in said at least one gas supply vessel in said gas box of the ion implanter during operation including dispensing of fluid therefrom.

9. The ion implanter of claim 8, wherein each of said at least one gas supply vessel contains fluid selected from the group consisting of arsine, phosphine, boron trifluoride, germanium tetrafluoride and silicon tetrafluoride.

10. The ion implanter of claim 8, wherein each of the at least one gas supply vessel is adapted to dispense said fluid at subatmospheric pressure.

11. The ion implanter of claim 8, wherein each of the at least one gas supply vessel contains a sorbent for storing the fluid and from which gas is selectively desorbed for dispensing from the vessel.

12. The ion implanter of claim 11, wherein said sorbent comprises carbon adsorbent.

13. The ion implanter of claim 8, wherein each of the at least one gas supply vessel contains a pressure regulator interiorly disposed therein.

14. A remote monitoring system for gas inventory in a gas box of an ion implanter, comprising a monitoring assembly in the gas box, and an output assembly external to the implanter, linked to the monitoring assembly by an optical cable, in which the gas box contains an adsorbent-based gas supply vessel, and the monitoring system is arranged with the monitoring assembly adapted to monitor gas box temperature and pressure of gas available from the gas supply vessel, and to transmit corresponding monitoring data through the optical cable to the output assembly, and with the output assembly configured to determine from the transmitted monitoring data, using isotherm equations for the adsorbent and gas in the vessel, the gas inventory remaining in the adsorbent-based gas supply vessel, and to display a graphical depiction of the gas inventory remaining in the adsorbent-based gas supply vessel.

15. The monitoring system of claim 3, wherein the at least one characteristic of the gas supply vessel is the vessel wall strain and the fluid is contained at high pressure in the vessel.

16. The monitoring system of claim 15, wherein the fluid is confined against a pressure regulator set to a predetermined set point pressure for dispensing of fluid from the vessel.

17. The monitoring system of claim 1, further comprising a monitor adapted for monitoring a pressure-reducing device.

* * * * *

UNITED STATES PATENT AND TRADEMARK OFFICE
CERTIFICATE OF CORRECTION

PATENT NO. : 9,097,611 B2  
APPLICATION NO. : 13/155237  
DATED : August 4, 2015  
INVENTOR(S) : James V. McManus et al.

It is certified that error appears in the above-identified patent and that said Letters Patent is hereby corrected as shown below:

On the Title Page, Item 75: "James Dietz" should be -- James A. Dietz --.

Column 10, line 61: "of the fluid supply vessel" should be -- of the gas supply vessel --.

Column 10, line 64: "of the fluid supply vessel" should be -- of the gas supply vessel --.

Column 12, line 12: "operation including dispensing of fluid therefrom." should be
-- operation including dispensing of gas therefrom. --.

Column 12, line 18: "least one gas supply vessel is adapted to dispense said fluid at" should be
-- least one gas supply vessel is adapted to dispense said gas at --.

Signed and Sealed this
First Day of March, 2016

Michelle K. Lee
*Director of the United States Patent and Trademark Office*